United States Patent [19]
Born

[11] Patent Number: 5,616,116
[45] Date of Patent: Apr. 1, 1997

[54] STOMA PROTECTOR

[75] Inventor: Jerome G. Born, St. Paul, Minn.

[73] Assignee: Lisa Willey, Des Moines, Iowa; a part interest

[21] Appl. No.: 447,216

[22] Filed: May 22, 1995

[51] Int. Cl.⁶ ........................................................ A61F 2/02
[52] U.S. Cl. ................. 600/32; 128/207.16; 128/207.17; 128/DIG. 26; 128/207.14; 604/332
[58] Field of Search ................................... 604/332–338; 600/32, 15; 128/207.14, 207.16, 207.17, DIG. 26

[56] References Cited

U.S. PATENT DOCUMENTS

| | | | |
|---|---|---|---|
| 3,330,271 | 7/1967 | Hozier | 128/207.14 X |
| 3,585,997 | 6/1971 | Ancerewicz, Jr. | 604/338 |
| 4,095,587 | 6/1978 | Ishikawa | 600/15 |
| 4,592,750 | 6/1986 | Kay | 604/337 |
| 5,060,645 | 10/1991 | Russell | 128/207.17 X |

*Primary Examiner*—Angela D. Sykes
*Assistant Examiner*—Ryan Carter
*Attorney, Agent, or Firm*—Zarley, McKee, Thomte, Voorhees, & Sease

[57] ABSTRACT

A unisex stoma protection device comprises a plate having a screened aperture which is aligned to fit over a stoma to protect the stoma from airborne pollutants. The device is held in place on the neck due to the curvature of the plate and a chain which is attached to the plate and extends around the patient's neck. The plate traps moisture adjacent the stoma.

15 Claims, 2 Drawing Sheets

STOMA PROTECTOR

FIELD OF THE INVENTION

The present invention relates to medical devices, and in particular, a device and method for covering and protecting a stoma on a patient who has undergone a laryngectomy.

BACKGROUND OF THE INVENTION

The larynx constitutes the upper part of the respiratory track between the pharynx and the trachea. Due to injury or disease, most commonly cancer, a patient may have to undergo a laryngectomy, which is a surgical removal of part or all of the larynx. Normally when this occurs, an airway is made through the patient's neck in order to provide a breathing passage since the patient is usually unable to breath normally due to the loss of respiratory organs. The external opening in the patient's neck is known as a stoma.

Laryngectomies often provide patients with several problems and inconveniences. For instance, patients often have to wear a tube in the stoma for all or part of the day to prevent the stoma from shrinking or closing. In addition, the opening itself must be protected from the environment in terms of maintaining proper moisture in and around the stoma and protecting it from dirt, dust, bugs and other miscellaneous airborne pollutants. Further, the patient who has a stoma may be self-conscious about others seeing the stoma.

One attempt to solve the above-stated problems involves the use of a bib which is worn over the stoma. The bib serves the dual purpose of protecting the stoma from drying out from exposure to the air and also to hide the stoma. This device, however, has proven unsatisfactory in several respects. First, the bib can be extremely hot and uncomfortable. Secondly, if the patient has an accidental cough or sneeze, the bib can get soiled and require frequent changing, thus necessitating the patient to carry around spare bibs. Further, since the bib must be next to the stoma, it must be worn beneath other clothing that is also worn around the neck area which makes it difficult for the patient to quickly gain access to the stoma area, to change the bib for example, as well as making such clothing items as dress shirts and ties difficult to wear. Moreover, a bib, while effectively hiding the stoma, also tends to draw attention to the wearer and the patient's condition.

Therefore, a primary objective of the present invention is the provision of a novel stoma cover and protector.

Another objective of the present invention is the provision of a stoma protector which maintains moisture around the stoma.

Another objective of the present invention is the provision of a stoma protector which protects the stoma from dirt, dust, and other airborne pollutants.

A further objective of the present invention is the provision of a stoma protector which is attractive yet inconspicuous on the wearer.

Yet another objective of the present invention is the provision of a stoma protector which is economical to manufacture and convenient, durable, and safe to use.

These and other objectives will be apparent from the following description of the invention.

SUMMARY OF THE INVENTION

The stoma protector of the present invention, which is intended to be worn by both male and female laryngectomy patients, includes a plate which is curved to fit the shape of a patient's neck. The plate has an aperture which is covered by a screen attached to the inside of the plate. The aperture and screen is aligned to fit directly over the stoma. The plate serves to trap moisture around the stoma to keep it from drying out. The screen prevents dirt, dust, bugs and other airborne pollutants from entering the stoma. The screen also allows for proper air circulation in and around the stoma area.

The protector is secured in place on the stoma in two primary ways. First, the shape of the plate, which is curved to fit a patient's neck, helps to hold the plate in place. Secondly, a chain to be worn around the patient's neck is attached to the plate with the chain having a length sufficient to secure the plate and screen in position over the stoma. The chain also gives the protector the ornamental appearance of a necklace which serves to conceal the true function of the protector from others. Further, bars may be attached on opposite sides of the screen which help hold the screen in position over the stoma.

The protector can be decorated in a variety of ways to make it more attractive. For example, gem stones, etchings, charms, colors, etc. can be added. Further, the plate can also be used to display the patient's emergency medical information.

DETAILED DESCRIPTION OF THE PREFERRED EMBODIMENT

Figure 1:
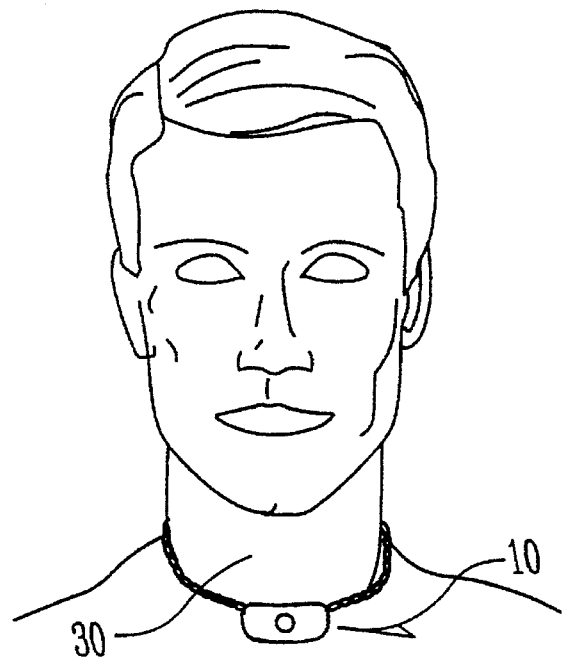
FIG. 1 is a perspective view of a stoma protector in accordance with the present invention as it is worn on the neck of a patient having a stoma.
Figure 2:
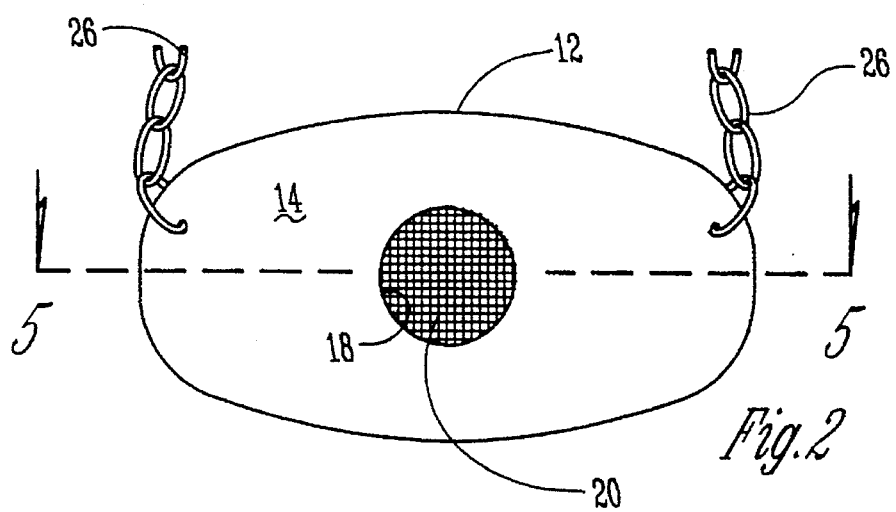
FIG. 2 is a front elevational view of the stoma protector.
Figure 3:
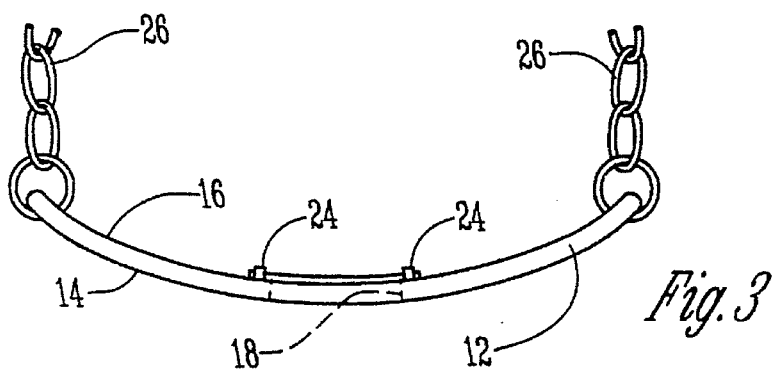
FIG. 3 is a side elevational view of the stoma protector.
Figure 4:
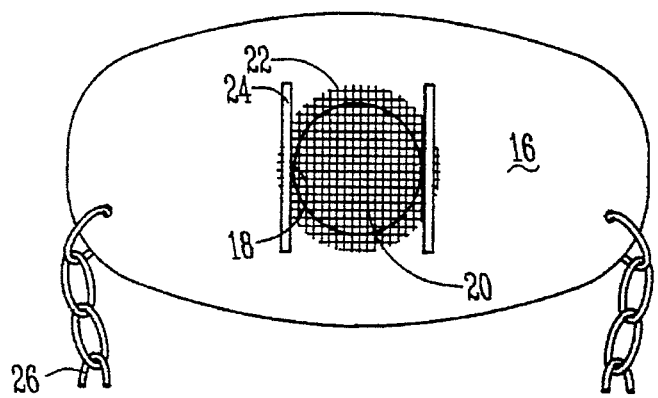
FIG. 4 is a back elevational view of the stoma protector.
Figure 5:
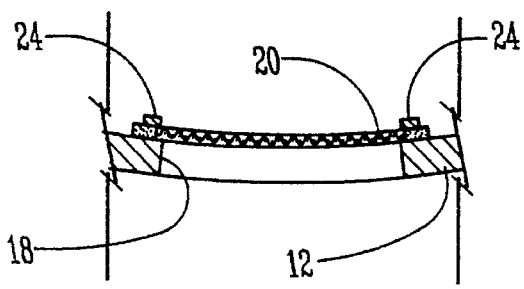
FIG. 5 is a sectional view of the stoma protector taken along lines 5—5 of FIG. 2.

The stoma protector of the present invention is generally designated in the drawings by the reference numeral 10. The stoma protector includes a plate 12 having a front surface 14, a rear surface 16, and a centrally positioned aperture 18. A screen 20 is attached to the rear surface 16 of the plate in any convenient manner, such as with an adhesive or solder. The screen 20 has a perimeter edge 22 which extends beyond the edge of the aperture 18, as best seen in FIG. 4. A pair of bars 24 are secured to the rear surface 16 of the plate 12 and overlap the edge 22 of the screen 20. Alternatively, the screen 20 may be secured to the bars 24, which in turn are secured to the rear surface of the plate using conventional means such as soldering, gluing, welding, etc. A chain or necklace 26 is attached to the plate 12, to allow the plate to be worn with the aperture 18 overlying the stoma. The bars 24 serve to hold the screen 20 in place and also constitute spaced apart projections on the rear surface 16 of the plate 12 which act to help hold the device in place over the stoma in the patient's neck 30 by engaging opposite sides of the stoma.

The plate 12 is curved to fit the shape of a patient's neck 30, which helps hold the plate 12 in place on the neck 30. The plate 12 also traps moisture around the stoma. The screen 20 covers the aperture 18 which allows the stoma to "breathe". The screen 20 also prevents dirt and other airborne particles from contaminating the stoma.

The plate 12 can be manufactured out of a variety of substances including gold, platinum, silver, surgical steel, other metals, plastic and wood. Metals that react with the skin are less desirable, such as copper which may turn the skin green. In addition, the plate 12 can come in many different sizes and shapes. For example, while the drawings show the plate 12 to be generally oblong in shape, the perimeter edge of the plate may be a polygonal, asymmetrical, or an abstract shape. The plate 12 is preferably oblong since it is the shape which best holds the plate 12 in place and allows the plate 12 to slide without exposing the stoma. The plate 12 is preferably not circular in shape since it does not keep the plate 12 in place as well and may tend to flip or slide. The aperture 20, while preferably circular in shape as shown in the drawings, may have other shapes. The shape of the plate 12 must be such that the patient has freedom of movement without the plate cutting into or hurting the neck 30.

Figure 6:
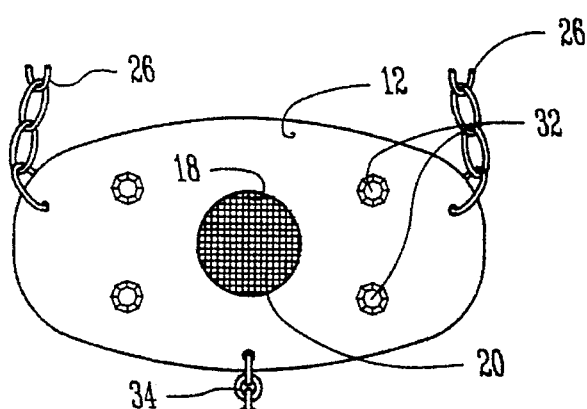
FIG. 6 is a front elevational view of a modified embodiment of a stoma protector having decorative ornamentation.

The plate 12 may also be decorated in a variety of ways. For instance, the plate 12 can be colored, etched, or gemstones 32 may be attached or embedded into the plate 12, as seen in FIG. 6. Moreover, a clasp 34 or clasps may be attached to the bottom of the plate 12 with or without a secondary chain 36 which may be used for holding charms, such as a cross 38. In this way, the stoma protector 10 is not only functional, but is also a stylish necklace. The chain 26 also makes the device more attractive and inconspicuous in that it gives the stoma protector 10 the appearance of a necklace.

Further, since patients who have undergone a laryngectomy often have other health-related problems, it is may be desirable for the patient to wear his/her medical information in case of an accident or emergency. A medical identification "charm" can be easily attached with clasps 34 to the bottom of plate 12 or the medical information can be etched directly onto the front or rear surface of the plate 12.

Figure 7:
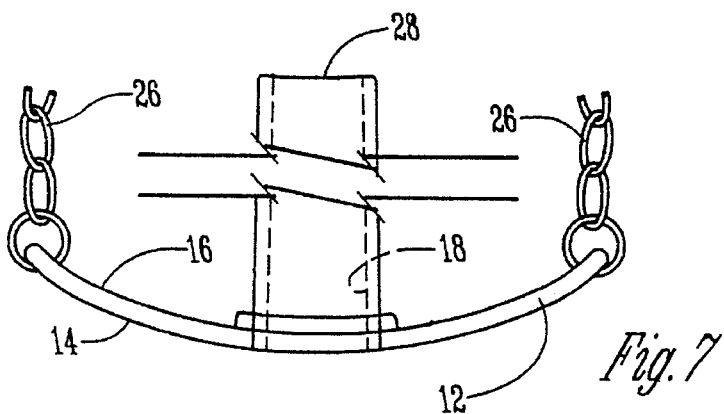
FIG. 7 is a side elevational view of a second modified embodiment having a tube thereon.

Laryngectomy patients often have to wear a tube which is inserted into the stoma in order to keep the stoma from shrinking or closing. Such a tube 28 could be attached to the plate 12 with or without the screen 20 by conventional means, as shown in the modified embodiment of FIG. 7.

Moreover, since patients who have undergone laryngectomies often have difficulty relearning how to talk, some patients use a servox, which is similar to a microphone. A servox can be easily used in conjunction with the protector 10 of the present invention without interfering with the function of the protector or the servox.

In addition, the protector 10 can be quickly and easily removed and rinsed off if it becomes soiled or for general cleaning purposes, unlike a conventional bib. A bib could also be worn over the protector 10 if needed, such as when the patient is outside in extremely cold weather.

The invention has been shown and described above in connection with the preferred embodiment, and it is understood that many modifications, substitutions, and additions may be made which are within the intended broad scope of the invention. From the foregoing, it can be seen that the present invention accomplishes at least all of the stated objectives.

What is claimed is:

1. A stoma protector for use by a person having a stoma from a laryngectomy, comprising:
    a curved plate having an aperture which is aligned to overlie a stoma, wherein said plate has forward and rearward surfaces;
    spaced apart projections on the rearward surface of the plate to maintain the plate in position over the stoma;
    a screen mounted on the rearward surface of the plate in covering relation to the aperture so as to allow breathing through the aperture; and
    a chain attached to the plate, the chain having a length sufficient to extend around a person's neck so as to hold the plate in place over the stoma.

2. The stoma protector of claim 1 wherein the plate has a smooth perimeter edge.

3. The stoma protector of claim 1 wherein the plate is oblong in shape so as to facilitate the positioning of the protector over the stoma.

4. The stoma protector of claim 1 wherein the projections are elongated bars having opposite ends secured to the rearward surface of the plate.

5. The stoma protector of claim 1 further comprising a charm attached to the plate.

6. The stoma protector of claim 1 wherein the plate has opposite forward and rearward surfaces, and further comprising decorative ornamentation on the forward surface of the plate.

7. The stoma protector of claim 1 further comprising a tube extending rearwardly from the plate, the tube being insertable into the stoma.

8. A method of protecting a stoma in a person's neck, the method comprising:
    placing a plate having an aperture against the person's neck such that the aperture overlies the stoma;
    extending projections rearwardly from the plate for engagement with the stoma;
    providing a screen in covering relation over the aperture to permit passage of air to and from the stoma; and
    holding the plate in position with a necklace extending around the person's neck.

9. The method of claim 8 further comprising inserting a tube extending rearwardly from the plate into the stoma.

10. A laryngectomy stoma protector for a person having a laryngectomy, comprising:
    a necklace extending around the person's neck, and including a plate with a hole therein, the hole being positioned over the stoma, wherein the plate has opposite front and back surfaces with at least one projection on the back surface to maintain the plate in position over the stoma; and
    a screen attached to the plate and extending over the hole to permit inhaling and exhaling through the stoma and hole of the plate.

11. The stoma protector of claim 10 wherein the plate has a curved profile to matingly engage the person's neck.

12. The stoma protector of claim 10 wherein the plate has a smooth perimeter edge.

13. The stoma protector of claim 7 further comprising a tube extending rearwardly from the plate, the tube being insertable into the stoma.

14. The stoma protector of claim 10 wherein the plate has opposite front and back surfaces, and the screen is attached to the back surface of the plate.

15. The stoma protector of claim 10 wherein the plate has a front surface with decorative ornamentation thereon.

* * * * *